US012678056B2

(12) United States Patent
Bhowmik et al.

(10) Patent No.: US 12,678,056 B2
(45) Date of Patent: Jul. 14, 2026

(54) EAR-WORN DEVICES FOR COMMUNICATION WITH MEDICAL DEVICES

(71) Applicant: Starkey Laboratories, Inc., Eden Prairie, MN (US)

(72) Inventors: Achintya Kumar Bhowmik, Cupertino, CA (US); Gregory John Haubrich, Champlin, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 1069 days.

(21) Appl. No.: 17/610,625

(22) PCT Filed: May 13, 2020

(86) PCT No.: PCT/US2020/032674
§ 371 (c)(1),
(2) Date: Nov. 11, 2021

(87) PCT Pub. No.: WO2020/232121
PCT Pub. Date: Nov. 19, 2020

(65) Prior Publication Data
US 2022/0304580 A1     Sep. 29, 2022

Related U.S. Application Data

(60) Provisional application No. 62/846,925, filed on May 13, 2019.

(51) Int. Cl.
*A61B 5/00* (2006.01)
*A61B 5/0205* (2006.01)
(Continued)

(52) U.S. Cl.
CPC ............ *A61B 5/0205* (2013.01); *A61B 5/002* (2013.01); *A61B 5/0022* (2013.01);
(Continued)

(58) Field of Classification Search
CPC .......... A61M 5/14244; A61M 5/14248; A61B 5/741; A61B 5/746; A61B 5/747; G16H 20/17
See application file for complete search history.

(56) References Cited

U.S. PATENT DOCUMENTS

| | | | |
|---|---|---|---|
| 5,653,735 | A | 8/1997 | Chen et al. |
| 6,461,331 | B1 | 10/2002 | Van Antwerp |

(Continued)

FOREIGN PATENT DOCUMENTS

| | | |
|---|---|---|
| EP | 3035710 | 6/2016 |
| WO | 2016116127 | 7/2016 |
| WO | 2020232121 | 11/2020 |

OTHER PUBLICATIONS

"International Preliminary Report on Patentability," for PCT Application No. PCT/US2020/032674 mailed Nov. 25, 2021 (8 pages).

(Continued)

*Primary Examiner* — Laura A Bouchelle
(74) *Attorney, Agent, or Firm* — Pauly, DeVries Smith & Deffner LLC

(57) ABSTRACT

Embodiments herein relate to medical device systems including ear-worn devices. In an embodiment, a medical device system includes an ear-worn device including a control circuit, a microphone in electrical communication with the control circuit, an electroacoustic transducer for generating sound in electrical communication with the control circuit, and a power supply circuit in electrical communication with the control circuit. The ear-worn device can be configured to received signals from a separate medical device and generate a notification using the received signals. Other embodiments are also included herein.

20 Claims, 13 Drawing Sheets

(51) Int. Cl.

| | |
|---|---|
| *A61B 5/021* | (2006.01) |
| *A61B 5/145* | (2006.01) |
| *A61K 9/70* | (2006.01) |
| *A61K 38/28* | (2006.01) |
| *A61N 1/39* | (2006.01) |
| *G16H 20/17* | (2018.01) |
| *A61M 5/142* | (2006.01) |
| *B60W 30/09* | (2012.01) |
| *H04R 1/10* | (2006.01) |

(52) U.S. Cl.

CPC ...... *A61B 5/02141* (2013.01); *A61B 5/14532* (2013.01); *A61B 5/6833* (2013.01); *A61B 5/741* (2013.01); *A61B 5/746* (2013.01); *A61B 5/747* (2013.01); *A61K 9/7023* (2013.01); *A61K 38/28* (2013.01); *A61N 1/3956* (2013.01); *G16H 20/17* (2018.01); *A61B 2503/22* (2013.01); *A61M 5/14244* (2013.01); *B60W 30/09* (2013.01); *B60W 2540/221* (2020.02); *H04R 1/1016* (2013.01)

(56) References Cited

U.S. PATENT DOCUMENTS

| | | | |
|---|---|---|---|
| 7,704,226 B2 | 4/2010 | Mueller et al. | |
| 7,806,886 B2 | 10/2010 | Kanderian et al. | |
| 7,875,022 B2 * | 1/2011 | Wenger ................... | G06F 16/60 |
| | | | 604/890.1 |
| 9,415,777 B2 | 8/2016 | Clarke et al. | |
| 9,452,259 B2 | 9/2016 | Dobbles et al. | |
| 9,720,907 B2 | 8/2017 | Bangalore et al. | |
| 9,867,539 B2 | 1/2018 | Heikenfeld et al. | |
| 10,136,831 B2 | 11/2018 | Heikenfeld | |
| 10,139,828 B2 | 11/2018 | Ho et al. | |
| 10,241,509 B1 | 3/2019 | Fields et al. | |
| 10,412,567 B1 * | 9/2019 | Tong ..................... | H04W 76/10 |
| 2008/0300572 A1 * | 12/2008 | Rankers ............. | A61B 5/14532 |
| | | | 604/504 |
| 2013/0343584 A1 | 12/2013 | Bennett et al. | |
| 2015/0057515 A1 | 2/2015 | Hagen et al. | |
| 2017/0172484 A1 | 6/2017 | Sonner et al. | |
| 2018/0035928 A1 | 2/2018 | Sonner et al. | |
| 2018/0263538 A1 | 9/2018 | Heikenfeld et al. | |
| 2018/0344223 A1 | 12/2018 | Heikenfeld | |
| 2019/0041345 A1 | 2/2019 | Nogueira et al. | |
| 2019/0059795 A1 | 2/2019 | Heikenfeld | |

OTHER PUBLICATIONS

"International Search Report and Written Opinion," for PCT Application No. PCT/US2020/032674 mailed Jul. 14, 2020 (12 pages).

"Communication under Article 94(3)," for European Application No. 20729537.9 (our file 371.0021WOEP) mailed May 22, 2025, 5 pages.

"Communication under Rules 161(1) and 162 EPC," for European Application No. 20729539.9 (our file No. 371.0021WOEP) mailed Dec. 21, 2021 (1 page).

"Reply to Communication under Article 94(3)," dated May 22, 2025, for European Application No. 20729537.9 (our file 371.0021WOEP) filed Nov. 24, 2025, 14 pages.

"Reply to Communication under Rules 161 and 162," dated Dec. 21, 2021, for European Patent Application No. 20729537.9 (our file 371.0021WOEP) file Jun. 28, 2022, 19 pages.

\* cited by examiner

EAR-WORN DEVICES FOR COMMUNICATION WITH MEDICAL DEVICES

This application is being filed as a PCT International Patent application on May 13, 2020, in the name of Starkey Laboratories, Inc., a U.S. national corporation, applicant for the designation of all countries, and Achintya Kumar Bhowmik, a U.S. Citizen, and Gregory John Haubrich, a U.S. Citizen, inventors for the designation of all countries, and claims priority to U.S. Provisional Patent Application No. 62/846,925, filed May 13, 2019, the contents of which are herein incorporated by reference in its entirety.

FIELD

Embodiments herein relate to ear-worn device that can communicate with various medical devices.

BACKGROUND

Many people have one or more medical devices to monitor their physiologic state and/or provide therapy. In some cases, such medical devices may be implanted. However, in other cases, such medical device can be external, such as those worn or adhered to the skin.

One type of medical device is an insulin pump. An insulin pump can be effective to treat diabetes through the delivery of basal insulin as well as periodic administration of insulin boluses. Insulin pumps and associated sensor devices can help provide effective control of blood glucose levels.

However, despite insulin treatment, blood glucose may still fall outside of a band of desirable concentrations. In addition, the supply of insulin within the insulin pump must be periodically replenished. As a result, some insulin pumps or pump systems can provide notifications relating to a patient's current blood glucose levels and/or a status of the pump system, such as being in need of additional insulin.

SUMMARY

In an embodiment, a medical device system includes an ear-worn device including a control circuit, a microphone in electrical communication with the control circuit, an electroacoustic transducer for generating sound in electrical communication with the control circuit, and a power supply circuit in electrical communication with the control circuit. The ear-worn device can be configured to received signals from a separate medical device and generate a notification using the received signals. Other embodiments are also included herein.

In an embodiment, the notification can include an alert or warning.

In an embodiment, the separate medical device can include a skin contact device configured for contact with the skin of the ear-worn device wearer.

In an embodiment, the separate medical device can include a continuous glucose monitoring (CGM) device.

In an embodiment, the signals from the separate medical device can be wireless signals and can include at least one of data regarding a remaining amount of an active agent in the separate medical device; data regarding a remaining battery life of the separate medical device; and data regarding a physiological state of the subject the separate medical device is associated with.

In an embodiment, the skin contact device can include a transdermal drug delivery patch. In an embodiment, the transdermal drug delivery device can include an active agent disposed therein. In an embodiment, the active agent can include insulin.

In an embodiment, a transdermal drug delivery device can include a polymeric matrix and an active agent disposed therein.

In an embodiment, the skin contact device can include a blood pressure monitoring patch.

In an embodiment, the separate medical device can include a battery-powered implantable medical device. In an embodiment, the implantable medical device includes at least one of a drug pump, a pacemaker, an implantable cardiac defibrillator (ICD), an implantable neuro or deep-brain stimulators, and implantable monitor, and an implantable sensor.

In an embodiment, the ear-worn device generates an alert through the electroacoustic transducer thereof using the data from the skin contact device.

In an embodiment, the ear-worn device classifies the alert into at least two categories, wherein a first category results in generating an alert only perceptible by the ear-worn device wearer and a second category results in generating an alert perceptible by an individual other than the ear-worn device wearer.

In an embodiment, the alert is only perceptible by the ear-worn device wearer is a speech-based alert.

In an embodiment, the alert is only perceptible by the ear-worn device wearer includes a status of the separate medical device or a consumable component thereof.

In an embodiment, the alert is only perceptible by the ear-worn device wearer includes a physiological status as measured by the separate medical device.

In an embodiment, the alert is only perceptible by the ear-worn device wearer includes a recommendation to schedule a medical appointment.

In an embodiment, the alert is only perceptible by the individual other than the ear-worn device wearer is conveyed through an ear-worn device accessory.

In an embodiment, the individual other than the ear-worn device wearer can include a care provider.

In an embodiment, classification is based on at least one of an emergency status of the alert; the age of the ear-worn device wearer; the functional status of the ear-worn device wearer; and the location of the ear-worn device wearer.

In an embodiment, the ear-worn device is configured to send a request for a medical product.

In an embodiment, the ear-worn device is configured to send a request for a consumable element to be sent.

In an embodiment, the separate medical device sends data to the ear-worn device through an ear-worn device accessory.

In an embodiment, the ear-worn device is configured to receive a command from the ear-worn device wearer and send a command to the separate medical device.

In an embodiment, the command can include a physiological parameter measurement interval.

In an embodiment, a notification can include a warning regarding an upcoming event that may result in a loss of an ear-worn device wearer's ability to operate a piece of equipment.

In an embodiment, a notification can include a warning regarding a possible onset of a seizure.

In an embodiment, a notification can include a warning regarding a planned defibrillation shock.

In an embodiment, the separate medical device can include an epilepsy treatment device or a cardiac treatment device. In an embodiment, the separate medical device can include an implanted epilepsy treatment device or an implanted cardiac treatment device.

In an embodiment, wherein a notification is sent to a piece of equipment. In an embodiment, the piece of equipment is a vehicle.

In an embodiment, the notification can include a command effective to cause a piece of equipment to enter a safe operation mode. In an embodiment, the notification can include a command effective to cause a vehicle to come to a stop or navigate to a safe location.

In an embodiment, a method of conveying signals from a medical device is included, the method including receiving a wireless signal from a medical device using an ear-worn device, the ear-worn device including a control circuit; a microphone in electrical communication with the control circuit; an electroacoustic transducer for generating sound in electrical communication with the control circuit; and a power supply circuit in electrical communication with the control circuit. The method further including evaluating the received wireless signal to determine an appropriate recipient and notification modality and sending a notification to the appropriate recipient regarding the received wireless signal.

In an embodiment, the notification can include at least one of an alert and a warning. In an embodiment, the alert or warning regarding at least one of a physiological state and a medical device state.

In an embodiment, evaluating the received wireless signal to determine an appropriate recipient can include determining an appropriate recipient category.

In an embodiment, the medical device can include a skin contact device.

In an embodiment, the medical device can include an insulin pump.

In an embodiment, the medical device can include a continuous glucose monitoring (CGM) device. In an embodiment, the ear-worn device can include a hearing assistance device.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

Embodiments of ear-worn devices described herein can both receive communications from and send communications to medical devices of various types including, but not limited to, implanted devices, skin contact devices (such as insulin pumps and skin-mounted patches), and the like. Embodiments of ear-worn devices described herein can also send communications in the form of notifications to the ear-worn device wearer and/or to third parties.

Ear-worn devices are unique because they can generate communications for the device wearer in a manner that only the device wearer is likely to perceive. For example, an ear-worn device can include a speaker positioned within the ear of the wearer that can provide an audio message at a volume that only the device wearer is likely to hear. This can be useful to maintain the privacy of the device wearer. However, there may also be other contexts (such as a critical alert regarding a life-threatening condition) where it may be desirable to generate the communication in such a way that third parties also can receive the communications. In various embodiments herein, ear-worn devices can generate and/or convey messages including, but not limited to, alerts and warnings to an ear-worn device wearer as well as to third parties intelligently based on context and the content of the messages.

Figure 1:
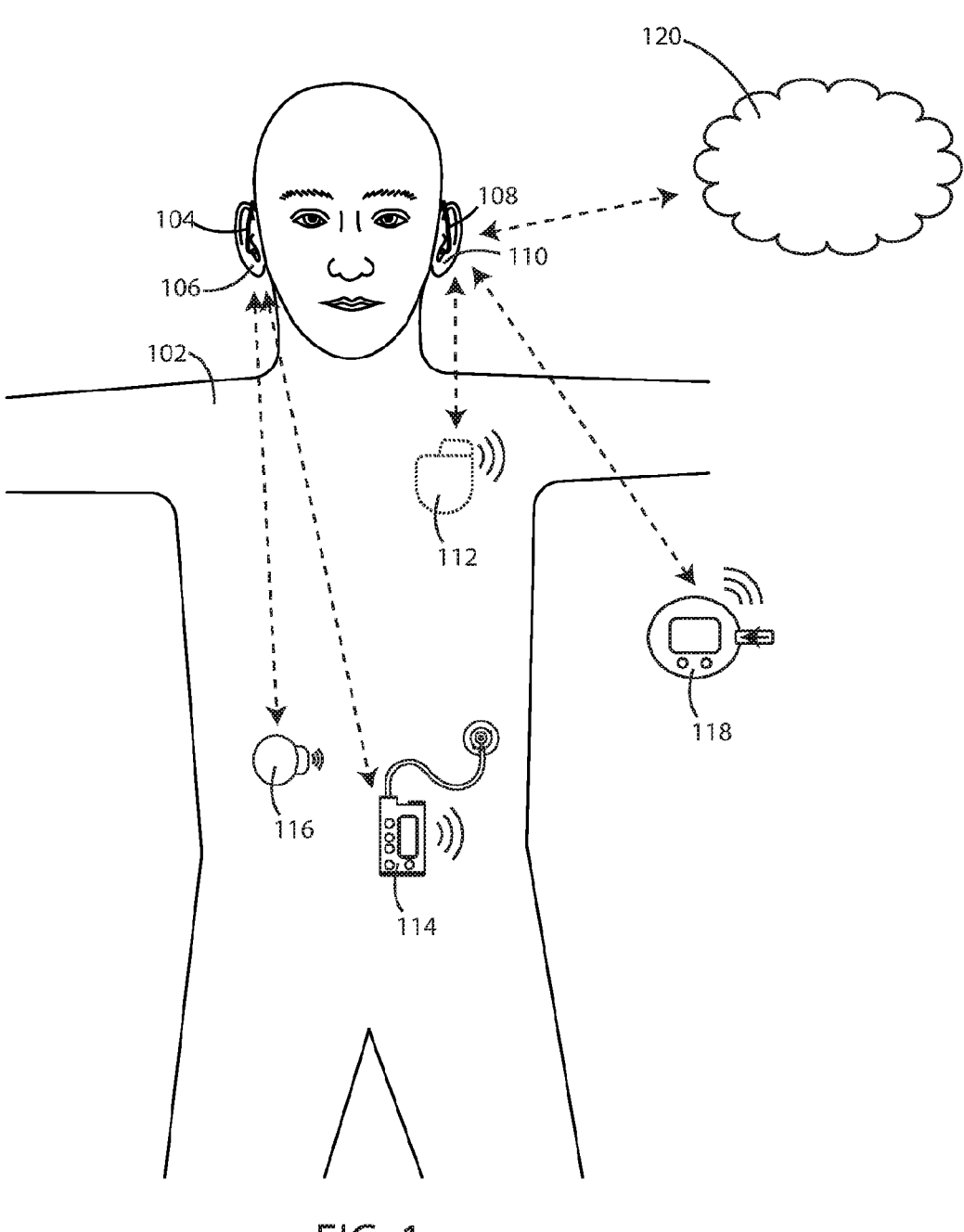
FIG. 1 is a schematic diagram of a patient with medical devices in communication with an ear-worn device in accordance with various embodiments herein.

Referring now to FIG. 1, a diagram is shown of a device wearer 102 with medical devices in communication with ear-worn device(s) in accordance with various embodiments herein. The medical devices can be implanted or non-implanted. For example, the medical devices can be fully implanted, partially implanted, external and skin-mounted, external and off-body, etc. There can be a single medical device in communication with the ear-worn device(s) or multiple medical devices (e.g., two, three, four, five, six, etc.). Thus, the device wearer 102 can have various medical devices that can include an implanted device 112 as well as external devices.

External devices can specifically include skin contact devices configured for contact with the skin of the device wearer 102. In some embodiments, the skin contact device could be a skin-mounted sensor device 116 such as a glucose sensor. In some embodiments, the skin contact device can be a skin-mounted patch, including, but not limited to, a transdermal drug delivery patch or a skin-mounted sensor patch. An exemplary skin-mounted sensor patch can include a skin-mounted glucose sensor and/or a skin-mounted blood pressure sensor such as a blood pressure monitoring patch. In various embodiments, a medical device herein (such as a skin-mounted device) can include a glucose sensor such as a continuous glucose monitor (CGM), such as a G6 CGM system commercially available from Dexcom, a LIBRE CGM system commercially available from Abbott, or a GUARDIAN Connect CGM system commercially available from Medtronic. Exemplary CGM devices include those described in U.S. Pat. Nos. 9,452,259, and 7,920,907, and U.S. Publ. Pat. Appl. No. 2019/0041345, the content of which is herein incorporated by reference.

Other skin-mounted sensors and/or sensor patches can include hydration sensors. Exemplary hydration and sweat sensing sensors and systems can include those described in U.S. Publ. Pat. Appl. Nos. 2015/0057515, 2018/0263538, 2019/0059795, 2017/0172484, 2018/0344223, 2018/0035928, and U.S. Pat. Nos. 10,136,831 and 9,867,539, the content of all of which are herein incorporated by reference.

As used herein, the term "skin-mounted" shall refer to a device or a portion thereof being held against the skin via various mechanisms including adhesives, mechanically (such as a strap or belt), or the like. In some embodiments, the skin contact device could be a device to administer a therapy, such as an insulin pump 114.

In some embodiments, the external device can be away from the skin, such as in the case of a test strip reader 118, which can analyze a sample of a bodily fluid such as blood for the presence and/or concentration of analytes such as glucose. Various other analytes are also contemplated herein.

The device wearer 102 can be wearing an ear-worn device 104 on or in their ear 106. In some embodiments, the device wearer 102 can also be wearing a second ear-worn device 108 on or in their other ear 110. However, it will be appreciated that scenarios where the device wearer 102 is only wearing a single ear-worn device are also contemplated herein. Exemplary ear-worn devices are described in greater detail below.

The medical devices (such as implanted device 112, insulin pump 114, skin-mounted sensor device 116, test strip reader 118, etc.) can send signals or communications wirelessly. The signals or communications can be electromagnetic frequency spectrum signals such as radio frequency signals, including 900 MHz signals, 2.4 GHz signals, IEEE 802.11 (e.g., WIFI®) communications or BLUETOOTH® (e.g., BLE, BLUETOOTH® 4.2 or 5.0) specification communications, and the like. In some embodiments, the signals or communications can be conveyed through an NFC (near-field communication) link such as that specified in Ecma-340, ISO/IEC 18092 or another short-range data communication protocol. In some embodiments, the signals or communications can be acoustic and include sounds generated by the medical devices, such as warning beeps, indicator sounds, and the like (see, e.g., U.S. Pat. No. 5,653,735, the content of which related to signaling sounds is herein incorporated by reference).

The signals or communications can include various things including, but not limited to, commands, queries, programming instructions, data for capture (which could be an event related to the device wearer). The signals or communications can include various pieces of information including, but not limited to, values for physiologic measures, notifications and/or warnings generated by the medical devices, medical device operational status, medical device consumable status, remaining life of the medical device, biometric data, and the like. In some embodiments, the consumable status can specific include a remaining amount of a therapeutic agent, such as a remaining amount of insulin within the device or a reservoir connected thereto. In some embodiments, the remaining life of the medical device can specifically include a remaining battery life. In some embodiments, the signals or communications can specifically include an acoustic low-battery notification which can be received with a microphone associated with the ear-worn device.

In some embodiments, the signals/data from the medical devices can specifically include at least one of data regarding a remaining amount of an active agent in the separate medical device, data regarding a remaining battery life of the separate medical device, and data regarding a physiological state of the subject the separate medical device is associated with.

In various embodiments herein, the signals sent from the medical devices can be received (directly or indirectly) by one or both of the ear-worn devices 104, 108. The ear-worn device(s) can take various steps in response to data received from the medical devices. In some embodiments, the ear-worn device(s) can convey (directly or indirectly) the data on another device or another node in the communication network. In some embodiments, the ear-worn devices 104, 108 can execute various procedures based on the signals and/or data sent from the medical devices.

Exemplary procedures/processing operations herein can include, but are not limited to, comparing signals as received at each ear-worn device, predicting a time until medical device or medical device component replacement is necessary, predicting a time until consumable replacement (including, but not limited to insulin cartridge replacement and/or reservoir replenishment), identifying a device status, identifying a current device operational state, comparing data against predetermined or dynamically determined threshold values, generating alerts or warnings if predetermined or dynamically determined conditions are met, data averaging, data time-averaging, statistical analysis, data normalizing, data aggregating, data sorting, deleting, data traversing, data encrypting, data decrypting, data transforming, data condensing (such as eliminating selected data and/or converting the data to a less granular form), data compressing (such as using a compression algorithm), merging, inserting, data time-stamping, data filtering, discarding outliers, calculating data trends and trendlines (linear, logarithmic, polynomial, power, exponential, moving average, etc.), and the like.

In various embodiments, the ear-worn device can generate a notification in the form an alert or warning using the wireless signals from the separate medical device. For example, the ear-worn device can evaluate the received wireless signals in order to identify a device status or a current operational state and then generate an alert or warning if the device status or current operation state falls within a category providing for an alert or warning. As another example, the ear-worn device can compare data against predetermined or dynamically determined threshold values and then generate alerts or warnings if the predetermined or dynamically determined conditions are met.

In some embodiments, the medical devices can send signals in response to a polling message or advertisement received from the ear-worn devices 104, 108. In other embodiments, the medical devices can send signals according to their own programming without first receiving a polling message or advertisement.

In some embodiments, the ear-worn device 104, 108 can also send data and/or signals wirelessly back to the medical devices or to the cloud 120 or to another device, person, and/or destination.

In some embodiments, the ear-worn device 104, 108 can be configured to receive a command from the ear-worn device wearer (which could be a spoken command received through a microphone, a gestural command such as a nod received through a motion sensor, or the like) and send or otherwise forward the command on to the appropriate medical device. In some cases, the command can be a configuration or programming command, such as specifying a physiological parameter measurement interval. In some cases, the command can specify changing an operational parameter of the medical device. Various commands are contemplated herein.

In some embodiments, the ear-worn device can be used to directly convey data, signals, communications, notifications and the like to other devices or out to the cloud or another data network. However, in some embodiments, an accessory to the ear-worn device can be used in order to assist in conveying data, signals, communications, notifications and the like. For example, an accessory to the ear-worn device can be used in order to assist in conveying data, signals, communications, notifications and the like to the cloud 120 or another data network. Thus, in some embodiments, the ear-worn device sends data, signals, communications, notifications and the like to other devices or layers (see, e.g., FIG. 3) through the ear-worn device accessory. In some embodiments, the medical device(s) can send data, signals, communications, notifications and the like to the ear-worn device through the ear-worn device accessory.

Figure 2:
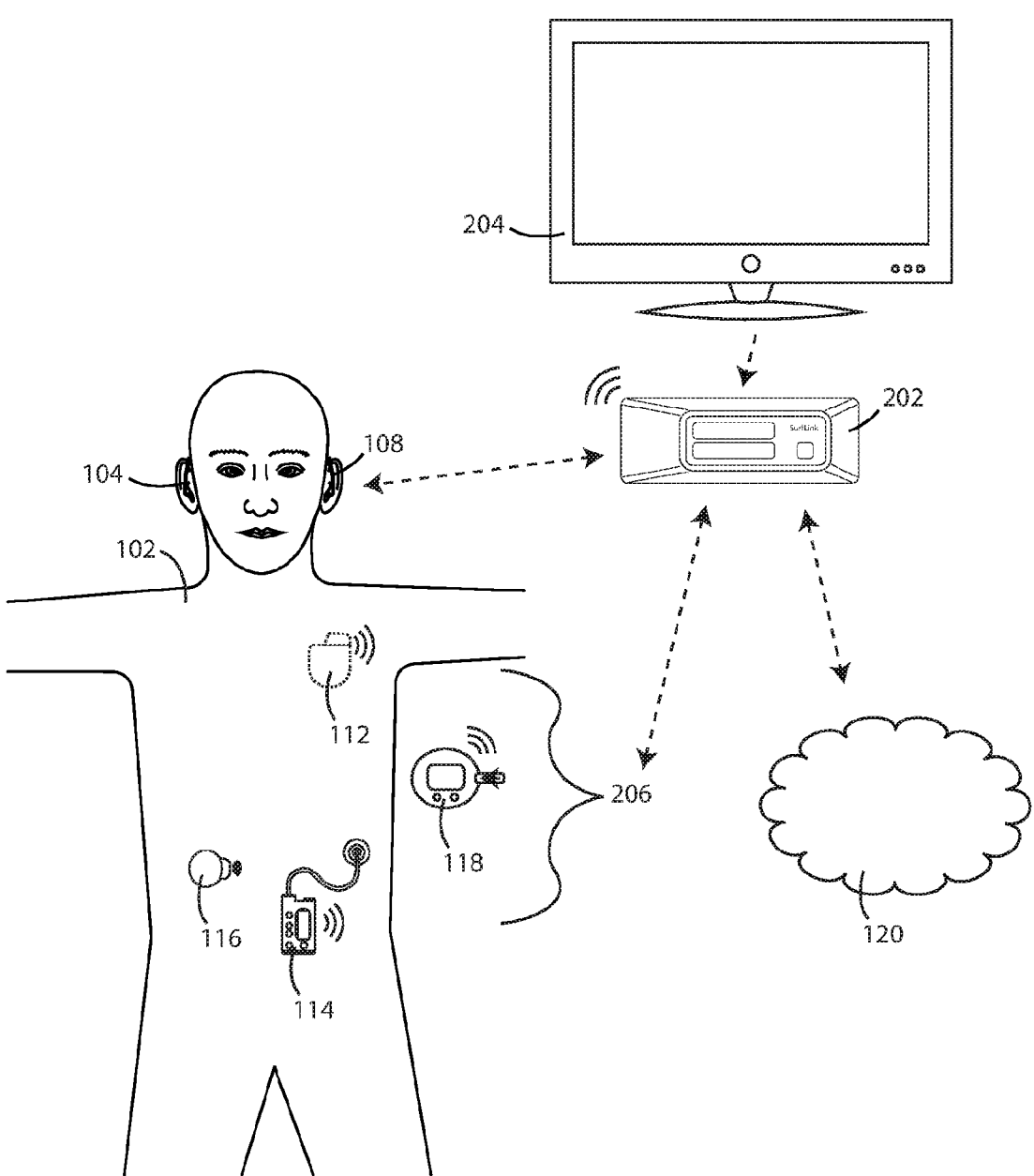
FIG. 2 is a schematic diagram of a patient with medical devices in communication with an ear-worn device accessory in accordance with various embodiments herein.

Referring now to FIG. 2, a diagram is shown of a device wearer 102 with medical devices 206 in communication with an ear-worn device accessory 202 in accordance with various embodiments herein. The medical devices 206 (which can include the types of medical devices previously described) can send data, signals, communications, notifications and the like to at least one of the ear-worn devices 104, 108 and/or can send data, signals, communications, notifications and the like to an accessory device 202. Various accessory devices are contemplated herein including, but not limited to a TV-streamer, a remote microphone, a remote-control device, a charging case, and the like. In some embodiments, the accessory device 202 can specifically be a TV-streamer which can serve to convey sound or signals reflecting sound from a television 204 or other device with an audio channel to at least one of the ear-worn devices 104, 108. However, the accessory device 202 can also send data, signals, communications, notifications and the like from the medical devices 206 on to the cloud or another data network.

Figure 3:
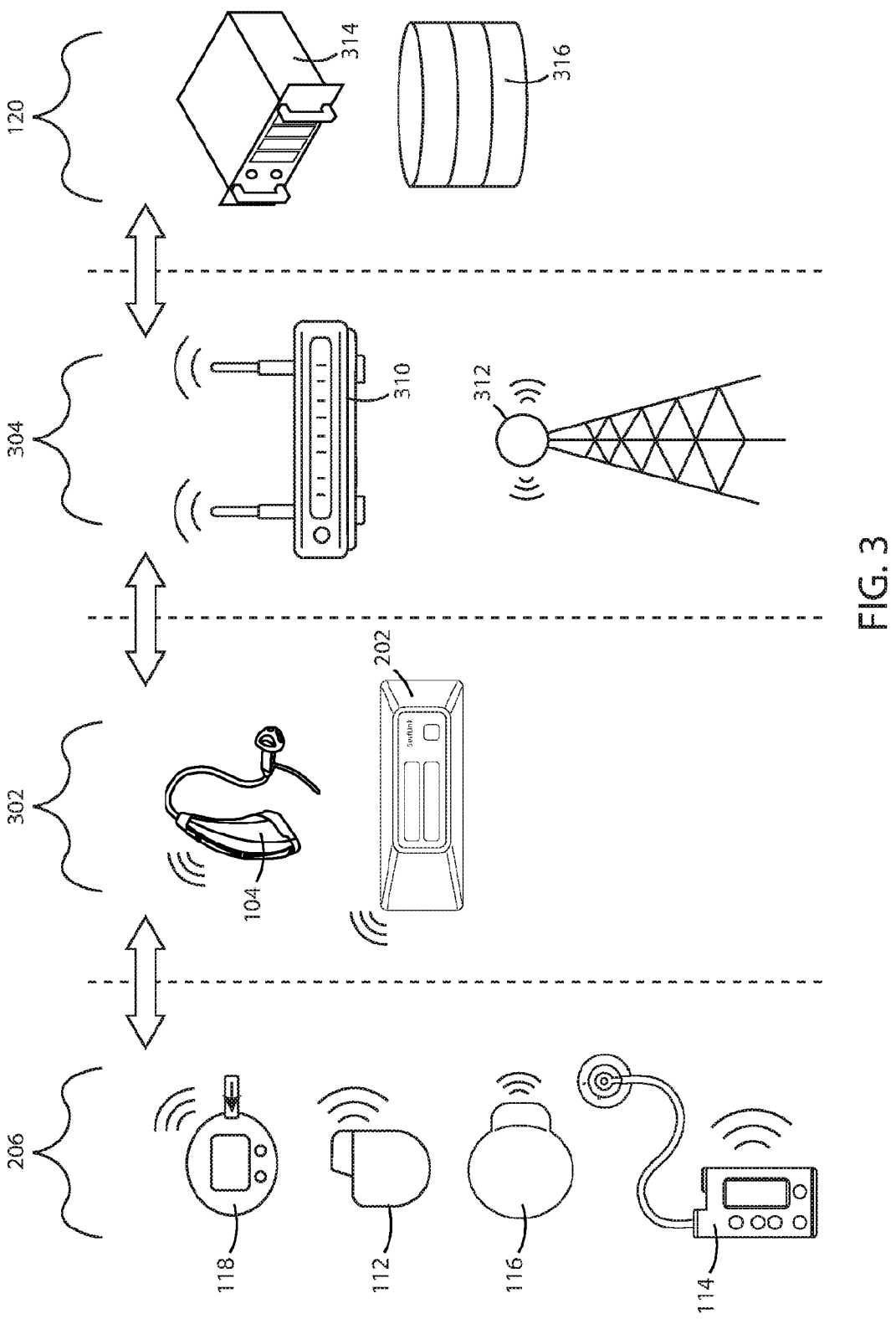
FIG. 3 is a schematic diagram of layers of a communication network including an ear-worn device/accessory in communication with medical devices in accordance with various embodiments herein.

In various embodiments herein, the communication network can be broken into layers with data, signals, communications, notifications and the like flowing between different layers of the network. Referring now to FIG. 3, a diagram is shown of layers of a communication network including an ear-worn device/accessory in communication with medical devices in accordance with various embodiments herein.

An exemplary medical device layer 206 can include medical devices (such as implanted device 112, insulin pump 114, skin-mounted sensor device 116, test strip reader 118, etc.) with sensors to gather information (including physiological information) as well as provide therapy. The medical devices can be implanted or non-implanted. The medical devices can be fully implanted, partially implanted, external and skin-mounted, external and off-body, etc. There can be a single medical device in addition to the ear-worn device(s) or multiple medical devices (e.g., two, three, four, five, six, etc.).

An exemplary ear-worn device/accessory layer 302 can include ear-worn devices generally such as ear-worn device 104 and, more specifically, hearing assistance devices of various types (as referenced above). The ear-worn device/accessory layer 302 can also include ear-worn device accessories such as ear-worn device accessory 202 and, more specifically, a TV-streamer, a remote microphone, a remote-control device, a charging case, and the like. The ear-worn device/accessory layer 302 can receive data, signals, communications, notifications and the like from the medical device layer 206. In some embodiments, the ear-worn device/accessory layer 302 can serve as a gateway through which all data, signals, communications, notifications and the like from the medical device layer 206 must pass before being passed (directly or after processing steps) on to a different layer of the communication network.

A data conveyance layer 304 can include elements such as a networking router 310 (or other networking hardware components) a wireless communications transmission tower 312 (which could be, for example, a cellular communications tower), as well as other hardware and/or software components. In various embodiments, the ear-worn device/accessory layer 302 can send data communications (data, signals, communications, notifications and the like) to the data conveyance layer 304. Likewise, the data conveyance layer 304 can send data communications back to the ear-worn device/accessory layer 302.

An exemplary cloud layer 120 can include various components for the transmission, storage, and/or processing of data including, but not limited to, server(s) 314 (real or virtual), database(s) 316, networking equipment (switches, routers, etc.) and the like. The data conveyance layer 304 can pass data along to the cloud layer 120. Similarly, data can be passed from the cloud layer 120 to the data conveyance layer 304. In some cases, the cloud layer 120 can serve as a bridge to other layers, devices, or individuals in order to receive the data, and provide data (such as data responsive to the received data in the form of instructions, commands, etc.) in return.

Figure 4:
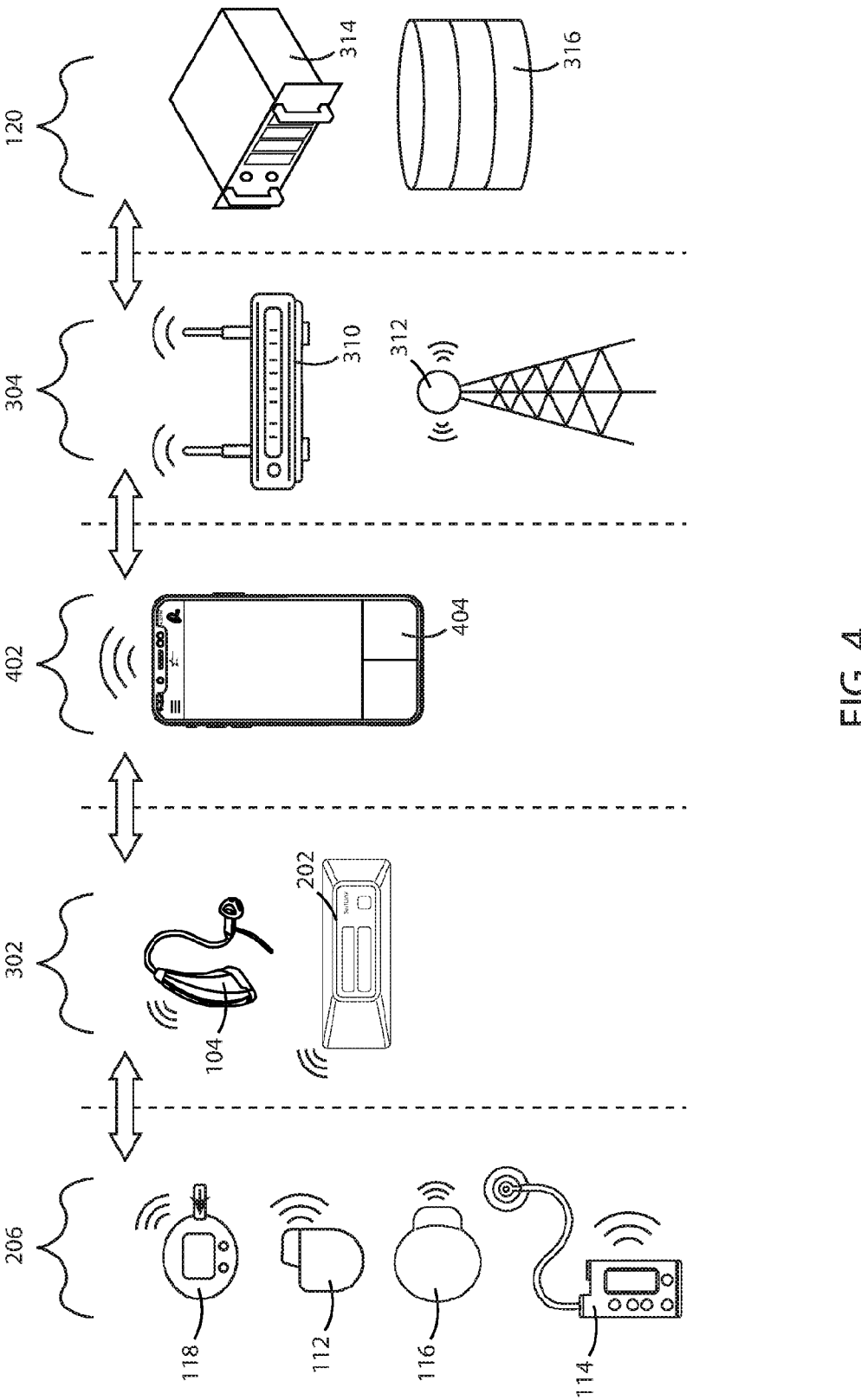
FIG. 4 is a schematic diagram of layers of a communication network including an ear-worn device/accessory in communication with medical devices in accordance with various embodiments herein.

It will be appreciated that in various embodiments, data, signals, communications, notifications and the like can pass through or between more layers than that illustrated with regard to FIG. 3. Referring now to FIG. 4, a diagram is shown of layers of a communication network including an ear-worn device/accessory in communication with medical devices in accordance with various embodiments herein. In this example, data, signals, communications, notifications and the like from the ear-worn device/accessory layer 302 can pass to a personal communications/data processing device layer 402. In some embodiments, the personal communications/data processing device layer 402 can include devices that such as a smart phone 404 that can include a processor, a video display, speakers, a microphone, and one or more antennas for wireless communication. The personal communications/data processing device layer 402 can be in communication with the data conveyance layer 304.

Figure 5:
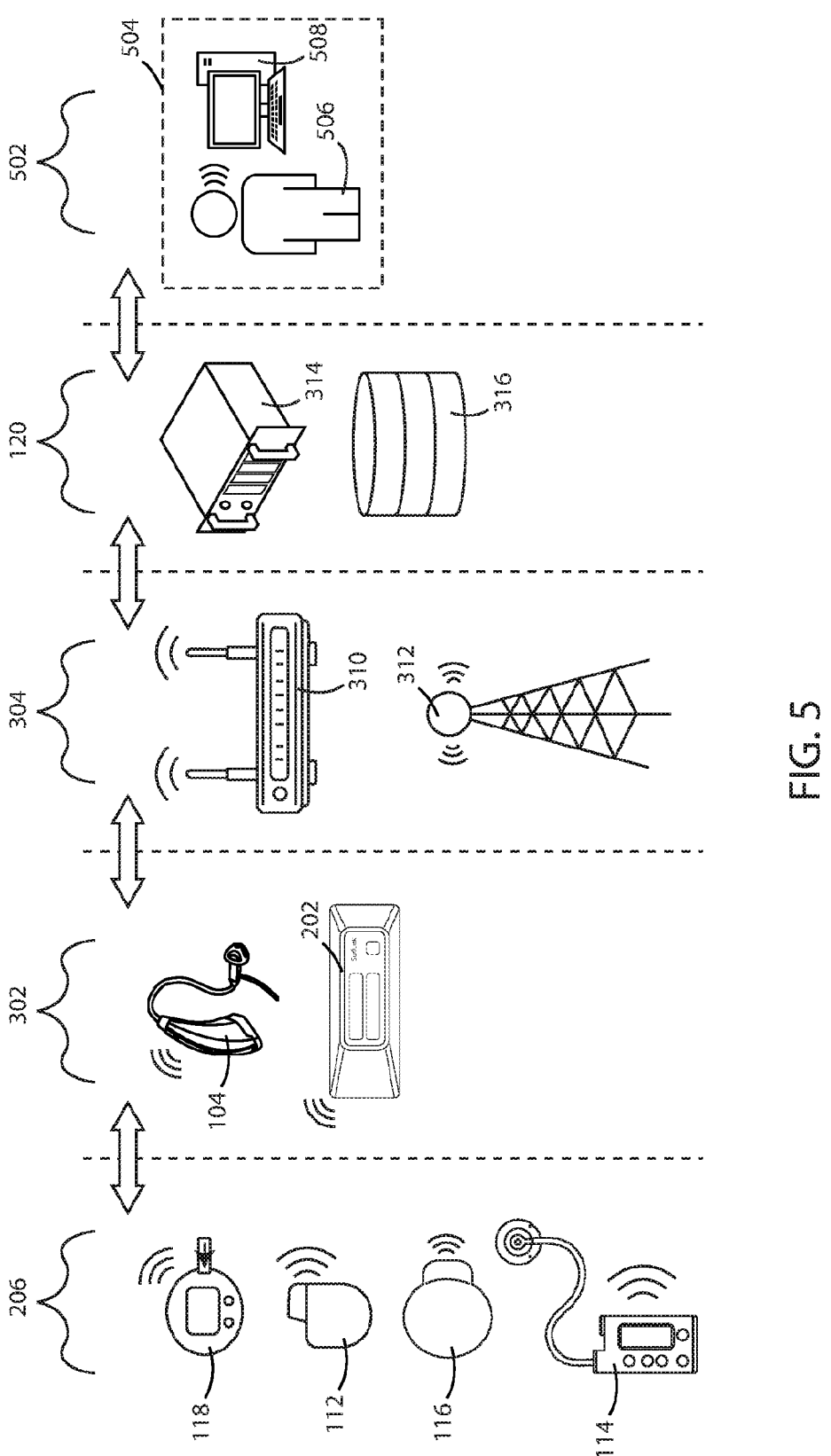
FIG. 5 is a schematic diagram of layers of a communication network including an ear-worn device/accessory in communication with medical devices and providing communication with a third party in accordance with various embodiments herein.

Referring now to FIG. 5, a diagram is shown of layers of a communication network including an ear-worn device/accessory in communication with medical devices and providing communication with a third party in accordance with various embodiments herein. In this example, the cloud layer 120 can facilitate communications with a remote care provider layer 502. The remote care provider layer 502 can include one or more of a remote environment 504, a care provider 506 (which could be a pharmacist, physician, physician's assistant, nurse, audiologist, other care provider, or the like) at the remote environment 504, and a computing device 508.

Figure 6:
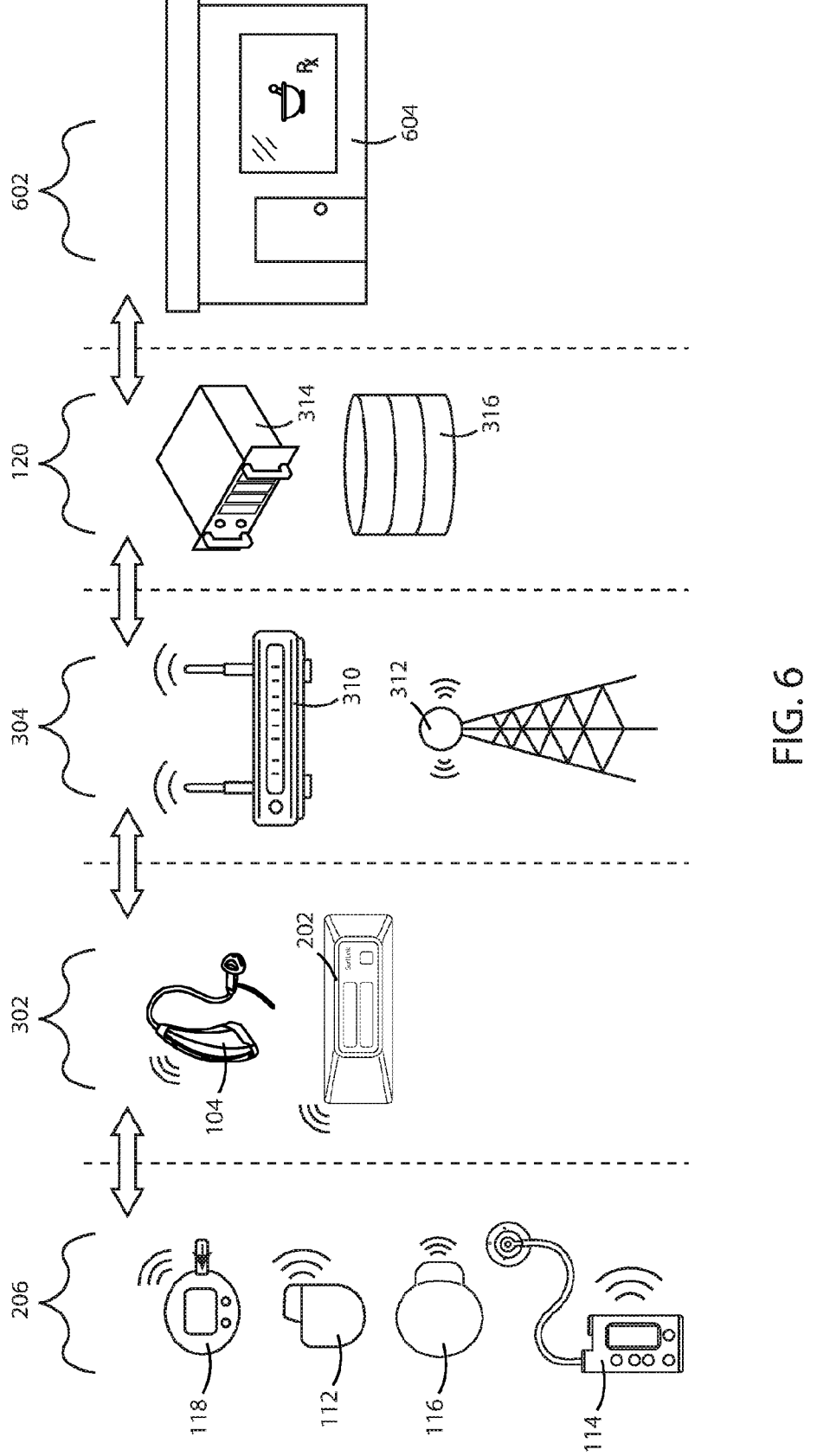
FIG. 6 is a schematic diagram of layers of a communication network including an ear-worn device/accessory in communication with medical devices and providing communication with a pharmacy in accordance with various embodiments herein.

Referring now to FIG. 6, a diagram is shown of layers of a communication network including an ear-worn device/accessory in communication with medical devices and providing communication with a pharmacy in accordance with various embodiments herein. In this example, the cloud layer 120 can facilitate communications with a product supply layer 602. In some embodiments, the product supply layer 602 can include a pharmacy 604 in order to provide medical products and/or consumables and other necessary supplies such as therapeutic agents including insulin, injectable hydrogels with active agents therein, anti-inflammatory agents, and the like. A medical product herein can include, but is not limited to, a drug, a therapy, a consumable, a supplement, or the like. In various embodiments, the ear-worn device can be configured to automatically send a request for additional consumable elements to the pharmacy 604 or other product supplier when the ear-worn device receives a communication from a medical device indicating that resupply is necessary.

In various embodiments, the ear-worn device or an accessory thereto can generate a notification such as an alert or warning using the wireless signals from the separate medical device. For example, the ear-worn device or an accessory thereto can evaluate the received wireless signals in order to identify a device status or a current operational state and then generate an alert or warning if the device status or current operation state falls within a category providing for an alert or warning. As another example, the ear-worn device or an accessory thereto can compare data against predetermined or dynamically determined threshold values and then generate alerts or warnings if the predetermined or dynamically determined conditions are met. In various embodiments herein, the ear-worn device or an accessory thereto can also determine an appropriate recipient and/or modality for the alert or warning. In some cases, the alerts or warnings can be provided in a discrete manner so as to only be received by the ear-worn device wearer. However, in some cases, the alerts or warning can be provided in a non-discrete manner so as to be perceived by both the ear-worn device wearer and those in the immediate vicinity and/or care providers and guardians that may be in the immediate vicinity or located remotely.

Figure 7:
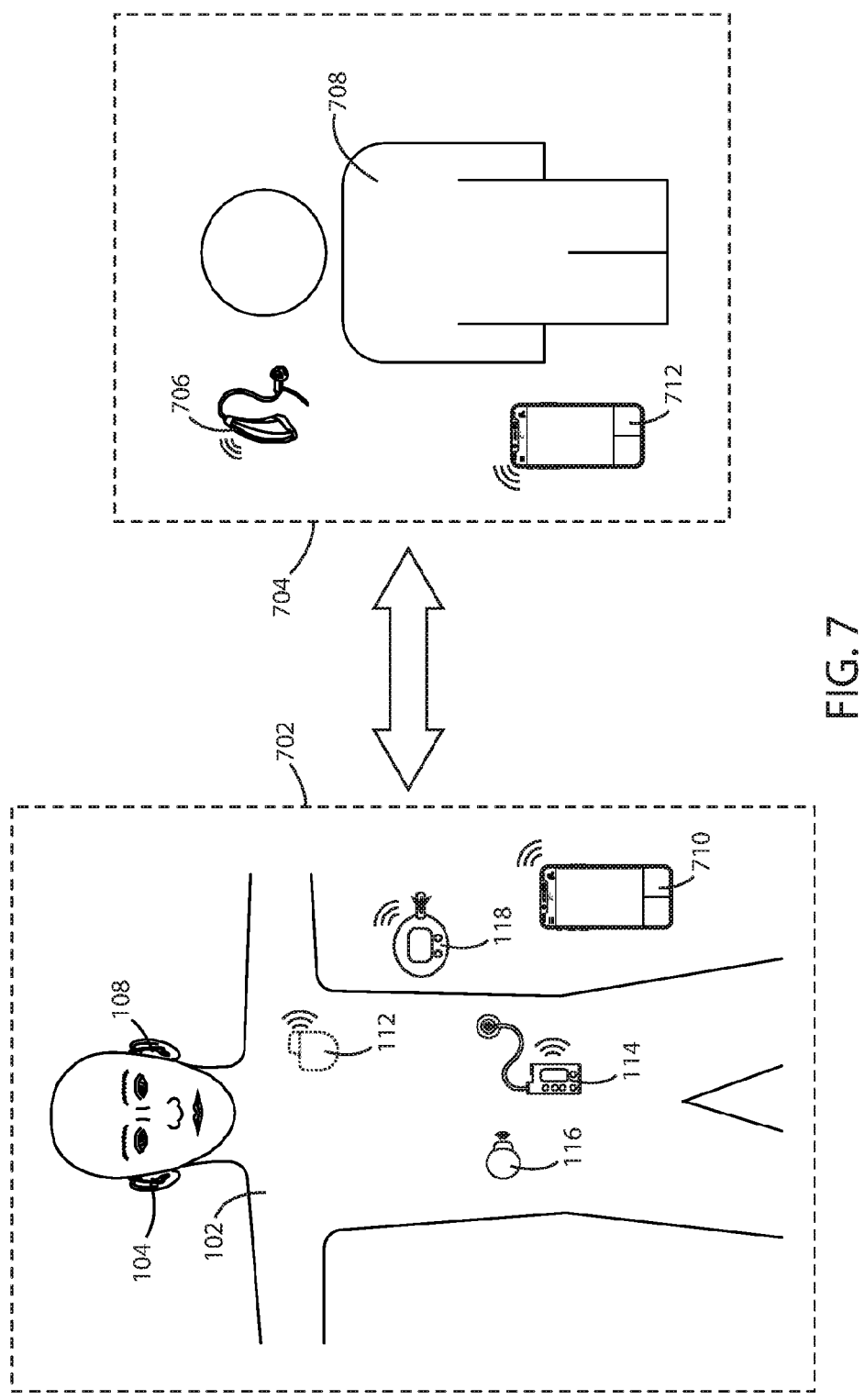
FIG. 7 is a schematic diagram of layers of a communication network including an ear-worn device/accessory in communication with medical devices and providing communication with a third party in accordance with various embodiments herein.

Referring now to FIG. 7, a diagram is shown of layers of a communication network including ear-worn devices 104, 108, in communication with medical devices 112, 114, 116, and 118 associated with an ear-worn device wearer 102 and providing communication with a third party 708 in accordance with various embodiments herein. In specific, the ear-worn device(s) 104, 108 can determine an appropriate recipient and then limit the alerts or warnings accordingly, such as by limiting the alerts or warnings to only a zone 702 associated with the ear-worn device wearer 102, only to a zone 704 associated with one or more third parties 708 (via a separate ear-worn device 706 of the third party 708 or another device 712 associated with the third party 708, or to multiple zones including both the zone 702 associated with the ear-worn device wearer and the zone 712 associated with one or more third parties 708. In various embodiments, a determination of who should receive the notification and/or how it should be conveyed can be based on at least one of an emergency status of the alert, the age of the ear-worn device wearer, the functional status of the ear-worn device wearer, and the location of the ear-worn device wearer.

Various factors can come into play when determining an appropriate recipient for a notification such as an alert or warning. In many cases, the appropriate recipient is simply the ear-worn device wearer. The alert or warning can be delivered to the ear-worn device wearer 102 using an electroacoustic transducer or speaker associated with the ear-worn device(s) 104, 108 or using a separate device 710 associated with the ear-worn device wearer 102. In various embodiments, the alert or warning can be provided through an electroacoustic transducer or speaker that is part of the ear-worn device 104, 108 itself and can be provided at a volume so that the alert or warning is discrete and only receivable by the ear-worn device wearer. In this manner, the alert or warning can be limited to the zone 702 associated with only the ear-worn device wearer. As such, information can be conveyed discretely to the ear-worn device wearer 102 without other people (even in the immediate vicinity of the ear-worn device wearer) being aware of the alert or warning.

By way of example, a notification regarding a recommendation to schedule a medical appointment may be something that is designated for receipt only by the ear-worn device wearer 102. However, in other embodiments, it may be appropriate to provide this type of notification to designated third parties.

In some cases, an urgency or importance of the alert or warning can be used as a factor to determine to whom and how to convey the alert or warning appropriately. For example, in some embodiments, if the alert or warning meets a threshold value for urgency or importance, then the ear-worn device 104, 108 may provide the alert or warning through communication channels that may also serve to notify third parties 708 (including or excluding those people in the immediate vicinity of the ear-worn device wearer 102). If, for example, a measured blood glucose level is dangerously high or low, then the device may provide an alert or warning not only through an electroacoustic transducer or speaker that is part of the ear-worn device 104, 108, but may trigger other devices to issue alerts or warnings through audio, visual, and/or haptic communication channels. The ear-worn device can trigger another device 710 (which could be a smartphone as one example) belonging to the ear-worn device wearer to issue a loud audible warning that can be heard by people in the immediate vicinity and/or a visual warning through a display screen. In this manner, if the ear-worn device wearer 102 were to suddenly become incapacitated before taking some corrective action, it would be more likely that someone nearby could be made aware of the situation so that they could render effective assistance.

In some embodiments, the status of the ear-worn device wearer 102 can be considered when determining how to issue alerts and/or warnings. For example, if the ear-worn device wearer is a minor or is an adult in a compromised state requiring specific care of a care-provider or guardian, then the ear-worn device can issue an alert or warning that is directed to a third party 708 (such as a care-provider or guardian) and not perceptible by the ear-worn device wearer 102. By way of example, it may be determined that the ear-worn device wearer 102 may be at risk of adverse reactions to stress generated by a warning or alert and/or they are sufficiently young or compromised, they may not be able to take effective responsive action anyhow. In these circumstances, the ear-worn device(s) 104, 108 may bypass providing an alert or warning to the ear-worn device wearer 102 and only provide such alerts or warnings to a third party 708 such as a care-provider or guardian through communications channels including audio, visual, and/or haptic channels. In some embodiments, the ear-worn device may still provide an alert or warning the ear-worn device wearer 102 as well as a third party 708 but provide different alerts or warnings to each. For example, the alert or warning provided to the ear-worn device 102 may be different in at least one of content, volume, pitch and speed and the alert or warning provided to a third party 708 such as a care-provider or guardian.

In accordance with some embodiments, the ear-worn device can classify the alert into a category (amongst two, three, four, five, six, seven or more categories) which then directs how and to whom to deliver the alert. For example, classification into a first category (see, e.g., category 1 in Table 1 below) can result in generating an alert only perceptible by the ear-worn device wearer and a different category (see, e.g., categories 2-4 in Table 1 below) can result in generating an alert perceptible by an individual other than the ear-worn device wearer. It will be appreciated that the categories shown in Table 1 below are merely exemplary and that various other categories are also contemplated herein.

TABLE 1

| CATEGORY | | | |
| --- | --- | --- | --- |
| 1. Wearer Only | 2. Wearer and Those in Immediate Vicinity | 3. Wearer and Designated Third Parties | 4. Designated Third Parties Only |

In various embodiments, a configuration table can be stored within the ear-worn device which maps particular types of notification and the appropriate zone (such as those described in FIG. 7) and/or appropriate category (such as those described in Table 1). Notification preferences/directives can be programmed in by the device-wearer or a third party. As manufactured, the device can include a configuration table that represents default values. An exemplary configuration table is shown below in Table 2. It will be appreciated, however, that the entries in the configuration table shown in Table 2 below are merely exemplary and that various other notification types and zones or categories are also contemplated herein.

TABLE 2

| NOTIFICATION CONFIGURATION TABLE | |
| --- | --- |
| NOTIFICATION TYPE | ZONE OR CATEGORY |
| Blood Glucose Out of Preferred Range | Zone: Wearer-Only; Category: 1 |
| Blood Glucose Dangerously Out of Preferred Range | Zone: Wearer and Third Parties; Category: 3 |
| Medical Appointment Recommended (Non-Emergency) | Zone: Wearer-Only; Category: 1 |
| Acute Medical Emergency | Zone: All; Categories 2&3 |

In some embodiments, notifications may relate to a predicted possible loss of control or possible loss of consciousness of the device wearer. For example, the notification can relate to a warning regarding an upcoming event that may result in a loss of an ear-worn device wearer's ability to operate a piece of equipment. The upcoming event can take various forms. In some embodiments, the event could be the predicted onset of a seizure. In such a scenario, an epilepsy monitoring and/or treatment device could detect physiological conditions that indicate a seizure is likely and a communication regarding this could be sent from the epilepsy monitoring and/or treatment to the ear-worn device. In some embodiments, the event could be a planned defibrillation shock. In such a scenario, a cardioverter-defibrillator could detect a heart rhythm requiring a defibrillation shock and could send a communication to the ear-worn device before administering the defibrillation shock. The ear-worn device then can send a notification on to the device wearer, one or more third parties, and various pieces of equipment. In some embodiments, a piece of equipment receiving such a notification automatically executes a process to achieve a safe-state. For example, if the device wearer is driving a vehicle, then a notification can be sent to the vehicle, which can engage a safe operation mode, such as a driving mode configured to safely bring the vehicle to a stop or auto-navigate the vehicle to a safe area. Aspects of autonomous vehicle navigation/control are described in U.S. Pat. Nos. 9,415,777, 10,241,509, and 10,139,828, the content of all of which are herein incorporated by reference.

Medical Devices

The medical devices can be implanted or non-implanted. The medical devices can be fully implanted, partially implanted, external and skin-mounted, external and off-body, etc. There can be a single medical device in addition to the ear-worn device(s) or multiple medical devices (e.g., two, three, four, five, six, etc.).

Figure 8:
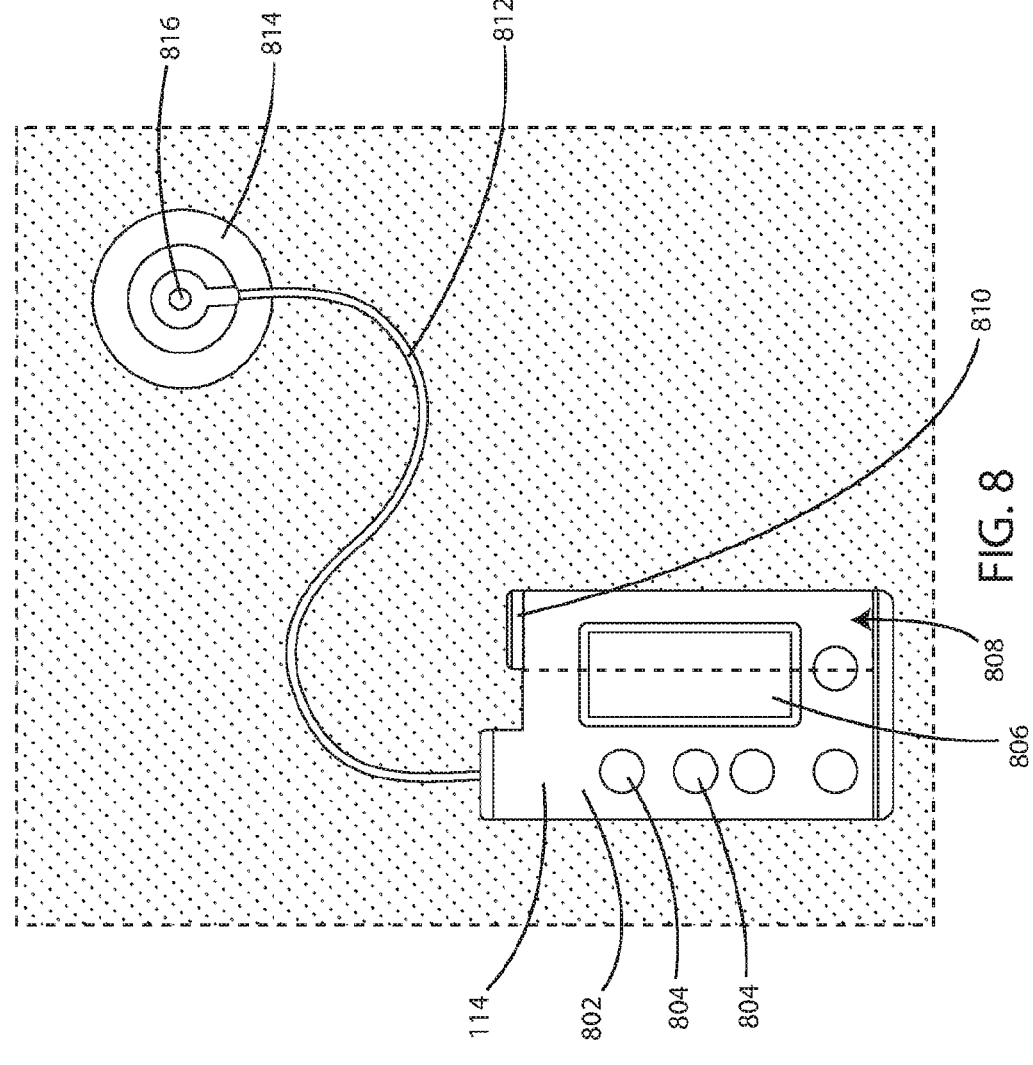
FIG. 8 is a schematic view of an exemplary medical device in accordance with various embodiments herein.

Referring now to FIG. 8, a schematic view is shown of an exemplary medical device in accordance with various embodiments herein. In this particular example, the medical device can be an insulin pump 114. The insulin pump 114 can include a pump housing 802 in fluid communication with a fluid transfer conduit 812 and an infusion patch/set 814. In some examples, one or more control buttons 804 can be disposed on the pump housing 802 (or another surface of the medical device) to allow for control input. In some embodiments, the insulin pump 114 can also include a display screen 806 to provide visual feedback. In various embodiments, a reservoir 808, can be disposed within or adjacent to the pump housing 802 and can be replenished by removing a reservoir cap 810 and then placing additional fluid containing an active agent (such as insulin) within the reservoir 808 or exchanging a cartridge or other container. In operation, a pump within the pump housing 802 can cause a fluid to move from the reservoir 808 through the fluid transfer conduit 812 and to the infusion patch/set 814 where it can then pass into a patient via a cannula 816 (or infusion needle). Notably, in some examples, the insulin pump 114 can include sensors to detect the remaining amount of fluid within the reservoir 808 and can also include a communications circuit and associated hardware such as an antenna in order to send and receive communications (wired or wireless). Communications can include, but are not limited to, information regarding the remaining amount of fluid within the reservoir 808, remaining battery life of the insulin pump 114, operational status of the insulin pump 114, data gathered and stored by the insulin pump 114 (such as records regarding fluid that has been delivered over a preceding time period including details such as basal amounts and bolus amounts and timing of the same), and the like. These communications can be received by an ear-worn device or accessory thereto as part of an ear-worn device/accessory layer 302 in accordance with various embodiments herein. Further details of exemplary medical devices for the delivery of insulin are found in U.S. Pat. Nos. 6,461,331; 7,704, 226; and 7,806,886, the content of which is herein incorporated by reference.

As used herein, the term "insulin", with regard to a therapeutic that is injected, infused, or otherwise delivered shall refer to insulin, an insulin mimetic, a small-molecule insulin mimetic, a peptide insulin mimetic, and the like.

Figure 9:
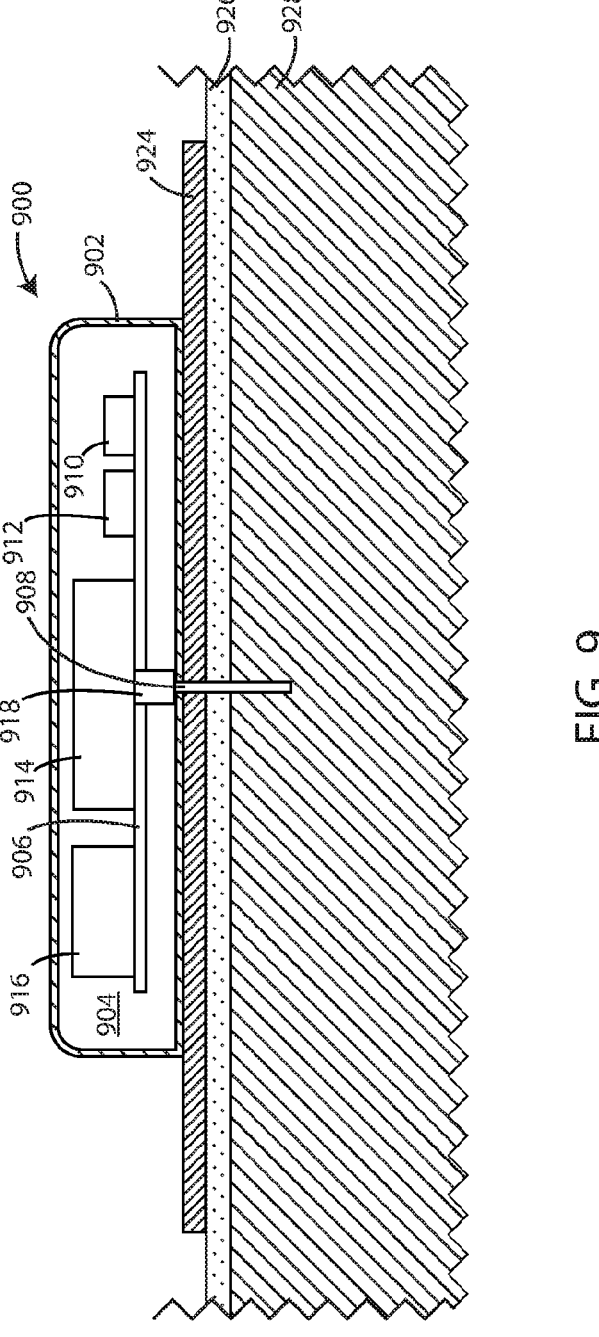
FIG. 9 is a cross-sectional view of a medical device in the form of a skin contact device in accordance with various embodiments herein.

Referring now to FIG. 9, a cross-sectional view is shown of a medical device 900 in accordance with various embodiments herein. The medical device 900 can serve as one example of a skin contact (or skin-mounted) device. The medical device 900 can include a housing 902 defining an interior volume 904. A circuit board 906 can be disposed within the interior volume 904. The circuit board 906 can serve to provide electronic communication between various components mounted thereon. In some embodiments, the circuit board 906 can also include a data bus for conveying data or other signals between components. The medical device 900 can include a control circuit 910 that can include one or more of a processor, memory, a timing circuit and the like. The control circuit 910 can control operations of the medical device 900. The medical device 900 can also include a communications circuit 912 that can include an antenna and other communication components such as one or more signal processors. The medical device 900 can use the communications circuit in order to generate communications, signals, alerts, warnings and the like. The medical device 900 can also include a power supply circuit 916 that can include a battery or capacitor as well as other power management components.

In some embodiments, the medical device 900 can include a therapeutic agent reservoir 914 and a pump 918 in order to deliver a therapeutic agent through a cannula 908 (or needle). In some embodiments, the medical device 900 can include an adhesive layer 924 in order to keep the medical device connected to the skin 926 of an individual. The cannula 908 can pass through the skin 926 into tissue 928 thereunder (which could be subcutaneous tissue, muscle tissue, connective tissue, adipose tissue, and the like) and thereby effectuate the transfer of a therapeutic agent to the tissue 928. However, in some embodiments, the cannula 908 can be used for withdrawal of a bodily fluid for testing, such as testing blood glucose levels, a level of a different analyte, of the like. In some embodiments, the cannula 908 can be used to provide fluid communication between the tissue 928 and a sensor that can be part of the medical device 900, such as a pressure sensor in order to measure blood pressure.

Figure 10:
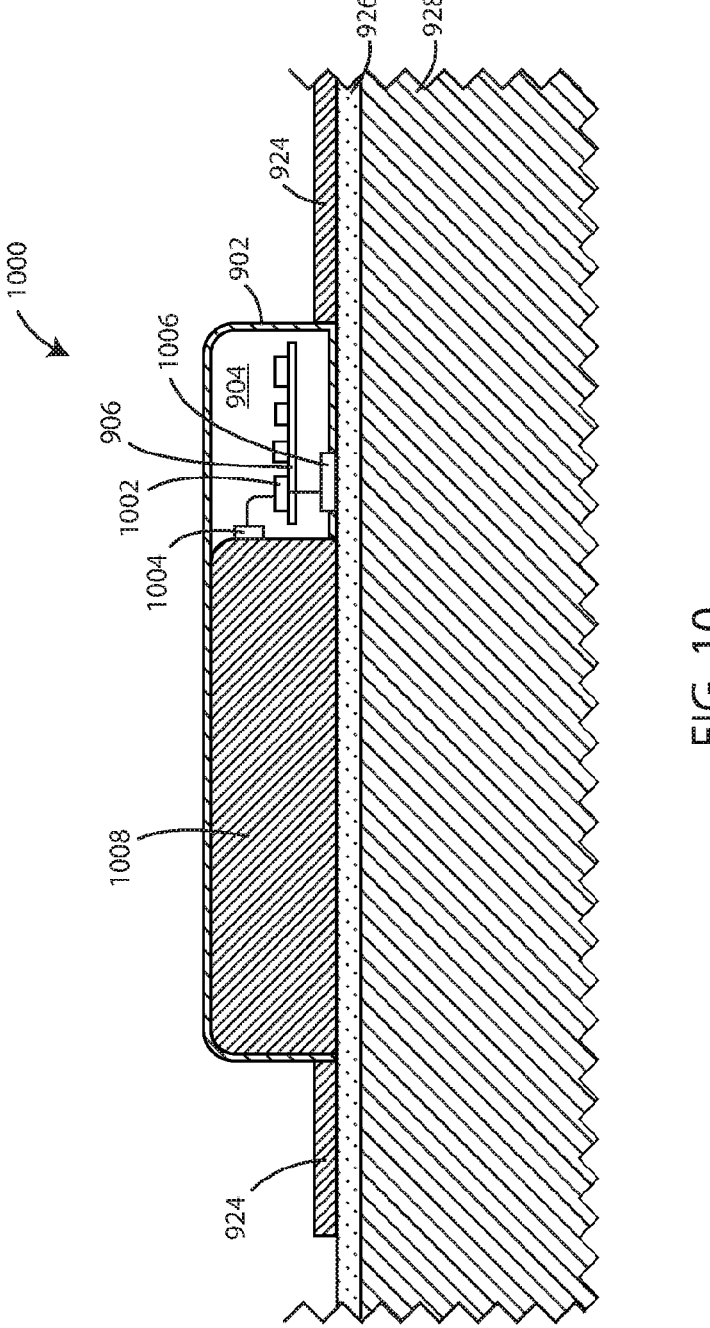
FIG. 10 is a cross-sectional view of a medical device in the form of a skin contact device in accordance with various embodiments herein.

Referring now to FIG. 10, a cross-sectional view is shown of a medical device 1000 in accordance with various embodiments herein. The medical device 1000 can serve as another example of a skin contact (or skin-mounted) device. The medical device 1000 can include many of the components described with respect to FIG. 9. However, in this embodiment, the therapeutic agent reservoir 914 can be in the form of a composition configured for direct transdermal delivery (migration) across the skin 926 and into the tissue 928. In some embodiments, the therapeutic agent reservoir 914 can include a polymeric matrix 1008 and a therapeutic agent disposed therein. In some embodiments, transdermal delivery (migration) can be passive (e.g., driven through diffusion). In other embodiments, transdermal delivery can be active, such as driven by a current or electrical potential. In some embodiments, electrode(s) 1004 can be in electrical communication with the therapeutic agent reservoir 914 to facilitate an electrical means of actively driving transdermal delivery. In some embodiments, electrode(s) 1006 can be in contact with the skin 926 for electrical sensing purposes and/or to facilitate delivering an electrical current for therapeutic or diagnostic purposes. In some embodiments, an electrical current delivery and/or electrical sensing control module 1002 can be in electrical communication with electrodes 1004, 1006 and the circuit board 906.

Ear-Worn Devices

In various embodiments, the ear-worn device can be a hearing assistance device. Hearing assistance devices herein can include, but are not limited to, behind-the-ear (BTE), in-the ear (ITE), in-the-canal (ITC), invisible-in-canal (IIC), receiver-in-canal (RIC), receiver in-the-ear (RITE) and completely-in-the-canal (CIC) type hearing assistance devices. In some embodiments, the hearing assistance device can be a hearing aid falling under 21 C.F.R. § 801.420. In another example, the ear-worn device can include one or more Personal Sound Amplification Products (PSAPs). In another example, the ear-worn device can include one or more cochlear implants, cochlear implant magnets, cochlear implant transducers, and cochlear implant processors. In another example, the ear-worn device can include one or more "hearable" devices that provide various types of functionality. In other examples, ear-worn device can include other types of devices that are wearable in, on, or in the vicinity of the user's ears. In other examples, ear-worn device can include other types of devices that are implanted or otherwise osseointegrated with the user's skull; wherein the ear-wearable device is able to facilitate stimulation of the wearer's ears via the bone conduction pathway.

Ear-worn devices, including hearing assistance devices (hearing aids and hearables (e.g., wearable earphones)), can, in various embodiments, include an enclosure, such as a housing or shell, within which internal components are disposed. Components of an ear-worn device herein can include a control circuit, digital signal processor (DSP), memory (such as non-volatile memory), power management circuitry, a data communications bus, one or more communication devices (e.g., a radio, a near-field magnetic induction device), one or more antennas, one or more microphones, a receiver/speaker (electroacoustic transducer), and various sensors as described in greater detail below. Various ear-worn devices herein can incorporate a long-range communication device, such as a BLUETOOTH® transceiver or other type of radio frequency (RF) transceiver.

Ear-worn devices of the present disclosure can incorporate an antenna arrangement coupled to a high-frequency radio, such as a 2.4 GHz radio. The radio can conform to an IEEE 802.11 (e.g., WIFI®) or BLUETOOTH® (e.g., BLE, BLUETOOTH® 4.2 or 5.0) specification, for example. It is understood that ear-worn devices of the present disclosure can employ other radios, such as a 900 MHz radio. Ear-worn devices of the present disclosure can be configured to receive streaming audio (e.g., digital audio data or files) from an electronic or digital source. Representative electronic/digital sources (also referred to herein as ear-worn device accessory devices) include an assistive listening system, a TV streamer, a remote microphone device, a remote control, or the like. In some embodiments, accessory devices herein can communicate with an ear-worn device using a proprietary data communication protocol. However, in other embodiments, the data communication protocol can be an established standard.

Figure 11:
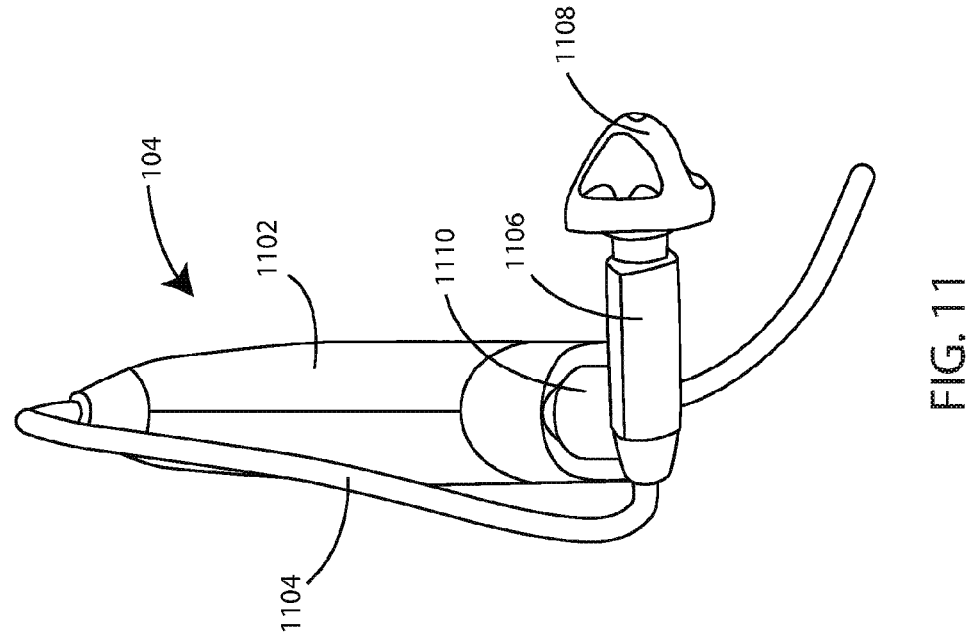
FIG. 11 is a schematic view of an ear-worn device in accordance with various embodiments herein.

Referring now to FIG. 11, a schematic view of an ear-worn device 104 is shown in accordance with various embodiments herein. The ear-worn device 104 can include a device housing 1102. The device housing 1102 can define a battery compartment 1110 into which a battery can be disposed to provide power to the device. The ear-worn device 104 can also include a receiver 1106 adjacent to an earbud 1108. The receiver 1106 can include a component that converts electrical impulses into sound, such as an electroacoustic transducer, speaker, or loud speaker. A cable 1104 or connecting wire can include one or more electrical conductors and provide electrical communication between components inside of the device housing 1102 and components inside of the receiver 1106.

Figure 12:
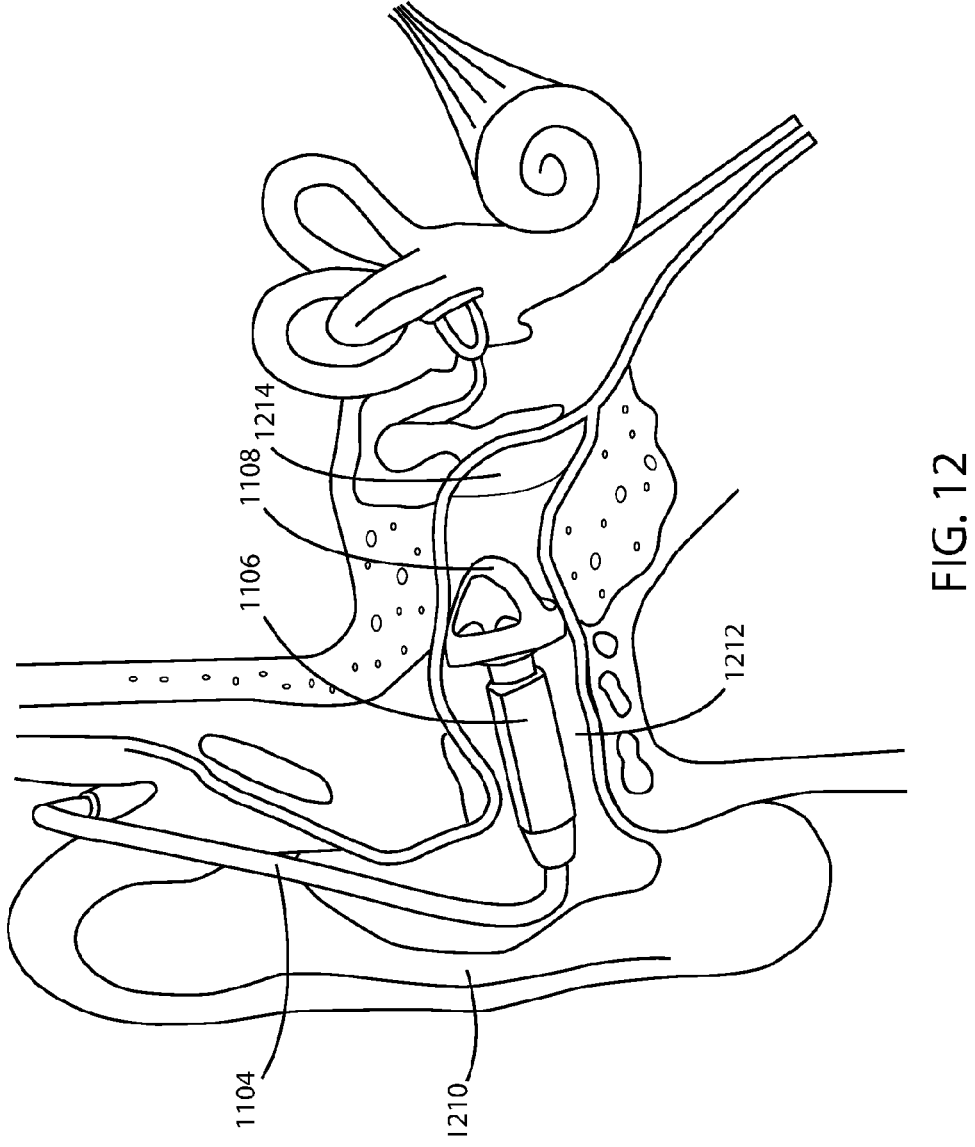
FIG. 12 is a schematic view of an ear-worn device partially placed within the ear canal of a subject in accordance with various embodiments herein.

Referring now to FIG. 12, a schematic view is shown of an ear-worn device partially disposed within the ear canal 1212 of a subject in accordance with various embodiments herein. In this view, the receiver 1106 and the earbud 1108 are both within the ear canal 1212, but do not directly contact the tympanic membrane 1214. The device housing is mostly obscured in this view behind the pinna 1210, but it can be seen that the cable 1104 passes over the top of the pinna 1210 and down to the entrance to the ear canal 1212.

Figure 13:
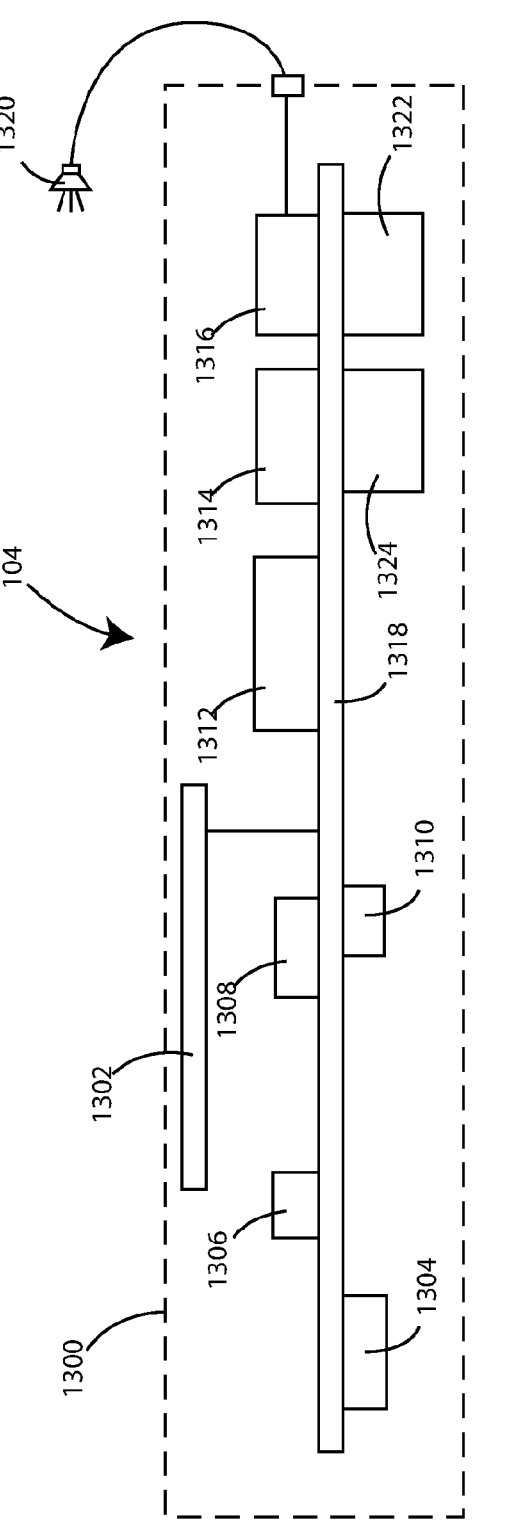
FIG. 13 is a schematic view of components of an ear-worn device in accordance with various embodiments herein.

Referring now to FIG. 13, a schematic block diagram is shown with various components of an ear-worn device 104 in accordance with various embodiments. The block diagram of FIG. 13 represents a generic ear-worn device for purposes of illustration. The ear-worn device 104 can include several components electrically connected to a mother circuit 1318 (e.g., flexible or non-flexible mother board) which is disposed within housing 1300. A power supply circuit 1304 can include a battery and can be electrically connected to the mother circuit 1318 and provides power to the various components of the ear-worn device 104. One or more microphones 1306 are electrically connected to the mother circuit 1318, which provides electrical communication between the microphones 1306 and a digital signal processor (DSP) 1312. Among other components, the DSP 1312 incorporates or is coupled to audio signal processing circuitry configured to implement various functions described herein. A sensor package 1314 can be coupled to the DSP 1312 via the mother circuit 1318. The sensor package 1314 can include one or more different specific types of sensors such as those described in greater detail below. In some embodiments, one or more user switches 1310 (e.g., on/off, volume, mic directional settings) are electrically coupled to the DSP 1312 via the mother circuit 1318.

An audio output device 1316 is electrically connected to the DSP 1312 via the mother circuit 1318. In some embodiments, the audio output device 1316 comprises a speaker (coupled to an amplifier). In other embodiments, the audio output device 1316 comprises an amplifier coupled to an external receiver 1320 adapted for positioning within an ear of a wearer. The external receiver 1320 can include an electroacoustic transducer, speaker, or loud speaker. The ear-worn device 104 may incorporate a communication device 1308 coupled to the mother circuit 1318 and to an antenna 1302 directly or indirectly via the mother circuit 1318. The communication device 1308 can be a BLUETOOTH® transceiver, such as a BLE (BLUETOOTH® low energy) transceiver or other transceiver (e.g., an IEEE 802.11 compliant device). The communication device 1308 can be configured to communicate with one or more external devices, such as those discussed previously, in accordance with various embodiments. In various embodiments, the communication device 1308 can be configured to communicate with an external visual display device such as a smart phone, a video display screen, a tablet, a computer, a virtual reality display device, an augmented reality display device, or the like.

In various embodiments, the ear-worn device 104 can also include a control circuit 1322 and a memory storage device 1324. The control circuit 1322 can be in electrical communication with other components of the device. The control circuit 1322 can execute various operations, such as those described herein. The control circuit 1322 can include various components including, but not limited to, a microprocessor, a microcontroller, an FPGA (field-programmable gate array) processing device, an ASIC (application specific integrated circuit), or the like. The memory storage device 1324 can include both volatile and non-volatile memory. The memory storage device 1324 can include ROM, RAM, flash memory, EEPROM, SSD devices, NAND chips, and the like. The memory storage device 1324 can be used to store data from sensors as described herein and/or processed data generated using data from sensors as described herein, including, but not limited to, information regarding therapy regimens, performance of the same, data regarding physiological properties, side-effects, and the like.

Sensors

Ear-worn devices as well as medical devices herein can include one or more sensor packages (including one or more discrete or integrated sensors) to provide data. The sensor package can comprise one or a multiplicity of sensors. In some embodiments, the sensor packages can include one or more motion sensors amongst other types of sensors. Motion sensors herein can include inertial measurement units (IMU), accelerometers, gyroscopes, barometers, altimeters, and the like. Motions sensors can be used to track movement of a patient in accordance with various embodiments herein.

In some embodiments, the motion sensors can be disposed in a fixed position with respect to the head of a patient, such as worn on or near the head or ears. In some embodiments, the motion sensors can be worn on or near another part of the body such as on a wrist, arm, or leg of the patient.

According to various embodiments, the sensor package can include one or more of an IMU, and accelerometer (3, 6, or 9 axis), a gyroscope, a barometer, an altimeter, a magnetometer, a magnetic sensor, an eye movement sensor, a pressure sensor, an acoustic sensor, a telecoil, a heart rate sensor, a global positioning system (GPS), a temperature sensor, a blood pressure sensor, an oxygen saturation sensor, an optical sensor, a blood glucose sensor (optical or otherwise), a galvanic skin response sensor, a cortisol level sensor (optical or otherwise), a microphone, acoustic sensor, an electrocardiogram (ECG) sensor, electroencephalography (EEG) sensor which can be a neurological sensor, eye movement sensor (e.g., electrooculogram (EOG) sensor), myographic potential electrode sensor (EMG), a heart rate monitor, a pulse oximeter, a wireless radio antenna, blood perfusion sensor, hydrometer, sweat sensor, cerumen sensor, air quality sensor, pupillometry sensor, cortisol level sensor, hematocrit sensor, light sensor, image sensor, and the like.

In some embodiments, the sensor package can be part of an ear-worn device. However, in some embodiments, the sensor packages can include one or more additional sensors that are external to an ear-worn device. For example, various of the sensors described above can be part of a wrist-worn or ankle-worn sensor package, or a sensor package supported by a chest strap.

Data produced by the sensor(s) of the sensor package can be operated on by a processor of the device or system.

As used herein the term "inertial measurement unit" or "IMU" shall refer to an electronic device that can generate signals related to a body's specific force and/or angular rate. IMUs herein can include one or more accelerometers (3, 6, or 9 axis) to detect linear acceleration and a gyroscope to detect rotational rate. In some embodiments, an IMU can also include a magnetometer to detect a magnetic field.

The eye movement sensor may be, for example, an electrooculographic (EOG) sensor, such as an EOG sensor disclosed in commonly owned U.S. Pat. No. 9,167,356, which is incorporated herein by reference. The pressure sensor can be, for example, a MEMS-based pressure sensor, a piezo-resistive pressure sensor, a flexion sensor, a strain sensor, a diaphragm-type sensor and the like.

The temperature sensor can be, for example, a thermistor (thermally sensitive resistor), a resistance temperature detector, a thermocouple, a semiconductor-based sensor, an infrared sensor, or the like.

The blood pressure sensor can be, for example, a pressure sensor. The heart rate sensor can be, for example, an electrical signal sensor, an acoustic sensor, a pressure sensor, an infrared sensor, an optical sensor, or the like.

The oxygen saturation sensor (such as a blood oximetry sensor) can be, for example, an optical sensor, an infrared sensor, or the like.

The electrical signal sensor can include two or more electrodes and can include circuitry to sense and record electrical signals including sensed electrical potentials and the magnitude thereof (according to Ohm's law where V=IR) as well as measure impedance from an applied electrical potential.

It will be appreciated that the sensor package can include one or more sensors that are external to the hearing assistance device. In addition to the external sensors discussed hereinabove, the sensor package can comprise a network of body sensors (such as those listed above) that sense movement of a multiplicity of body parts (e.g., arms, legs, torso). In some embodiments, the hearing assistance device can be in electronic communication with the sensors or processor of another medical device, e.g., an insulin pump device or a heart pacemaker device.

Methods

Many different methods are contemplated herein, including, but not limited to, methods of making, methods of using, and the like. Aspects of system/device operation described elsewhere herein can be performed as operations of one or more methods in accordance with various embodiments herein.

In various embodiments, a method of conveying signals from a medical device is included. The method can include receiving a wireless signal from a medical device using an ear-worn device. The ear-worn device can include, amongst other components, a control circuit, a microphone in electrical communication with the control circuit, an electroacoustic transducer for generating sound in electrical communication with the control circuit, and a power supply circuit in electrical communication with the control circuit. The method can further include evaluating the received wireless signal to determine an appropriate recipient and notification modality. The method can further include sending a notification to the appropriate recipient regarding the received wireless signal. The method can further include generating an alert regarding at least one of a physiological state and a medical device state.

In various embodiments, the notification can include at least one of an alert and a warning. In some embodiments, the alert or warning regarding at least one of a physiological state and a medical device state. In some embodiments of the method, evaluating the received wireless signal to determine an appropriate recipient can include determining an appropriate recipient category. In various embodiments, the medical device can include a skin contact device. In various embodiments, the medical device can include an insulin pump. In various embodiments, the ear-worn device can include a hearing assistance device.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A medical device system comprising:
an ear-worn device comprising
  a control circuit;
  a microphone in electrical communication with the control circuit;
  an electroacoustic transducer for generating sound in electrical communication with the control circuit; and
  a power supply circuit in electrical communication with the control circuit;
the ear-worn device configured to receive wireless signals from a separate medical device;
wherein the ear-worn device compares data from the wireless signals from the separate medical device against predetermined or dynamically determined threshold values and generates a notification when predetermined or dynamically determined conditions are met.

2. The medical device system of claim 1, the separate medical device comprising a skin contact device configured for contact with the skin of the ear-worn device wearer.

3. The medical device system of claim 1, the separate medical device comprising a continuous glucose monitoring (CGM) device.

4. The medical device system of claim 1, wherein the wireless signals from the separate medical device include at least one of:

data regarding a remaining amount of an active agent in the separate medical device;

data regarding a remaining battery life of the separate medical device; and data regarding a physiological state of a subject the separate medical device is associated with.

5. The medical device system of claim 2, the skin contact device comprising a transdermal drug delivery patch.

6. The medical device system of claim 2, wherein the ear-worn device generates an alert through the electroacoustic transducer thereof using data from the skin contact device.

7. The medical device system of claim 6, wherein the ear-worn device classifies the alert into at least two categories, wherein a first category results in generating an alert only perceptible by the ear-worn device wearer and a second category results in generating an alert perceptible by an individual other than the ear-worn device wearer.

8. The medical device system of claim 7, wherein the alert perceptible by the individual other than the ear-worn device wearer is conveyed through an ear-worn device accessory.

9. The medical device system of claim 7, the individual other than the ear-worn device wearer comprising a care provider.

10. The medical device system of claim 7, wherein classification is based on at least one of an emergency status of the alert;

an age of the ear-worn device wearer;

a functional status of the ear-worn device wearer; and a location of the ear-worn device wearer.

11. The medical device system of claim 1, wherein the ear-worn device is configured to send a request for a medical product.

12. The medical device system of claim 1, wherein the ear-worn device is configured to send a request for a consumable element to be sent.

13. The medical device system of claim 1, wherein the ear-worn device is configured to receive a command from the ear-worn device wearer and send a command to the separate medical device.

14. The medical device system of claim 13, the command comprising a physiological parameter measurement interval.

15. The medical device system of claim 1, the notification comprising a warning regarding an upcoming event that may result in a loss of an ear-worn device wearer's ability to operate a piece of equipment.

16. The medical device system of claim 1, the notification comprising a warning regarding a possible onset of a seizure.

17. The medical device system of claim 1, the notification comprising a warning regarding a planned defibrillation shock.

18. The medical device system of claim 1, the notification comprising a command effective to cause a piece of equipment to enter a safe operation mode.

19. The medical device system of claim 1, the notification comprising a command effective to cause a vehicle to come to a stop or navigate to a safe location.

20. A method of conveying signals from a medical device comprising:

receiving a wireless signal from a medical device using an ear-worn device, the ear-worn device comprising a control circuit;

a microphone in electrical communication with the control circuit;

an electroacoustic transducer for generating sound in electrical communication with the control circuit; and a power supply circuit in electrical communication with the control circuit;

evaluating the received wireless signal to determine an appropriate recipient and notification modality;

sending a notification to the appropriate recipient regarding the received wireless signal.

\* \* \* \* \*